(12) United States Patent
Young et al.

(10) Patent No.: US 7,578,183 B2
(45) Date of Patent: *Aug. 25, 2009

(54) ACOUSTIC VOLUME INDICATOR

(75) Inventors: Winston B. Young, San Dimas, CA (US); Huey Wai, Monrovia, CA (US)

(73) Assignee: Young Engineering & Manufacturing, Inc., San Dimas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/749,077

(22) Filed: May 15, 2007

(65) Prior Publication Data

US 2008/0115581 A1 May 22, 2008

Related U.S. Application Data

(63) Continuation of application No. 11/245,696, filed on Oct. 7, 2005, now Pat. No. 7,216,536, which is a continuation-in-part of application No. 11/200,252, filed on Aug. 8, 2005, now abandoned, which is a continuation of application No. 10/175,712, filed on Jun. 20, 2002, now Pat. No. 6,925,868.

(60) Provisional application No. 60/300,335, filed on Jun. 22, 2001.

(51) Int. Cl.
G01F 23/28 (2006.01)
G01F 17/00 (2006.01)

(52) U.S. Cl. .......................... 73/290 V; 73/149; 73/579

(58) Field of Classification Search .................. 73/579, 73/570, 149, 290 V, 290 R, 49.2, 32 A
See application file for complete search history.

(56) References Cited

U.S. PATENT DOCUMENTS

| | | | | | |
|---|---|---|---|---|---|
| 2,667,782 | A | * | 2/1954 | Shea | 73/149 |
| 2,924,096 | A | * | 2/1960 | Humphres | 73/149 |
| 3,413,847 | A | * | 12/1968 | Kraushaar | 73/149 |
| 3,596,510 | A | * | 8/1971 | Paine et al. | 73/149 |
| 3,624,826 | A | * | 11/1971 | Edwards | 73/149 |
| 4,122,429 | A | * | 10/1978 | Hatai | 367/108 |
| 4,599,892 | A | * | 7/1986 | Doshi | 73/49.2 |
| 4,635,487 | A | * | 1/1987 | Gowing | 73/854.62 |
| 4,715,221 | A | * | 12/1987 | Grims et al. | 73/149 |
| 4,991,433 | A | * | 2/1991 | Warnaka et al. | 73/290 V |
| 5,022,261 | A | * | 6/1991 | Wolfson et al. | 73/149 |
| 5,099,454 | A | * | 3/1992 | Dieulesaint et al. | 367/99 |
| 5,388,496 | A | | 2/1995 | Miller et al. | |

(Continued)

*Primary Examiner*—Helen C. Kwok
(74) *Attorney, Agent, or Firm*—Connolly Bove Lodge & Hutz LLP

(57) ABSTRACT

Acoustic volume indicators for determining liquid or gas volume within a container comprise a contactor to vibrate a container wall, a detector to receive vibration data from the container wall, a processor to convert vibration data to frequency information and compare the frequency information to characteristic container frequency vs. volume data to obtain the measured volume, and an indicator for displaying the measured volume. The processor may comprise a microprocessor disposed within a housing having lights that each represent a particular volume. The microprocessor is calibrated to provide an output signal to a light that indicates the container volume. The processor may comprise a computer and computer program that converts the data to frequency information, analyzes the frequency information to identify a peak frequency, compares the peak frequency to the characteristic frequency vs. volume data to determine the measured volume, and displays the measured volume on a video monitor.

19 Claims, 6 Drawing Sheets

U.S. PATENT DOCUMENTS

| | | |
|---|---|---|
| 5,396,827 A | 3/1995 | Miller et al. |
| 5,528,933 A * | 6/1996 | Nemirow ..................... 73/149 |
| 6,305,219 B1 * | 10/2001 | Bentz et al. ............... 73/290 V |
| 6,513,373 B1 * | 2/2003 | Home ........................ 73/149 |
| 6,615,657 B2 * | 9/2003 | Hongerholt et al. ....... 73/290 V |
| 6,925,868 B2 * | 8/2005 | Young et al. .............. 73/290 V |
| 7,216,536 B2 * | 5/2007 | Young et al. .............. 73/290 V |

* cited by examiner

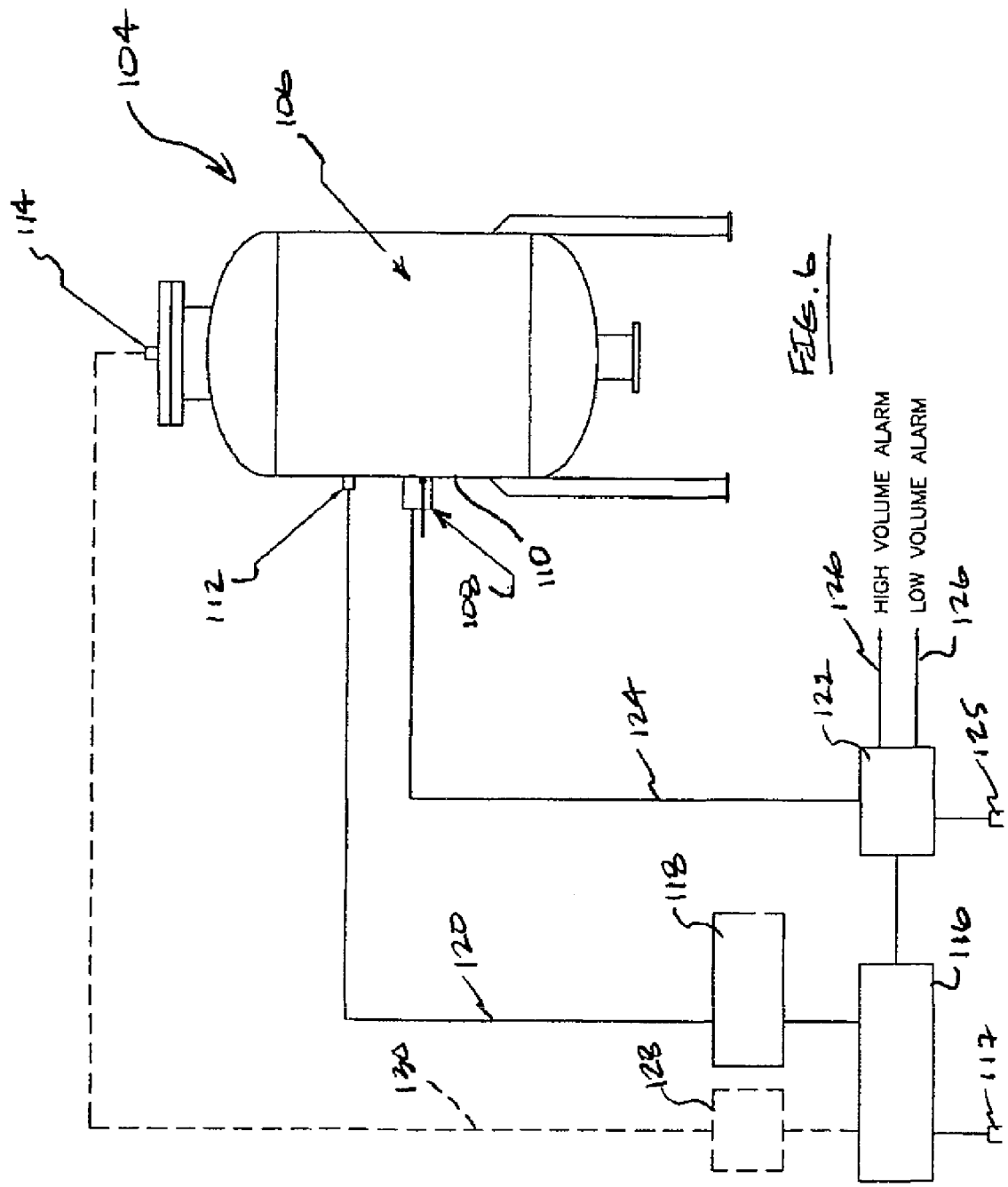

ACOUSTIC VOLUME INDICATOR

CROSS-REFERENCE TO RELATED APPLICATIONS

This application is a continuation of U.S. patent application Ser. No. 11/245,696 that was filed on Oct. 7, 2005, which is a continuation-in-part of U.S. patent application Ser. No. 11/200,252 that was filed on Aug. 8, 2005, that was a continuation of U.S. patent application Ser. No. 10/175,712, filed on Jun. 20, 2002, now U.S. Pat. No. 6,925,868, that claimed the benefit of U.S. Provisional Application No. 60/300,335, filed Jun. 22, 2001, which are all incorporated herein by reference.

FIELD OF THE INVENTION

This invention relates to devices and methods for using the same that are configured for measuring the volume of liquid or gas in a container and, more particularly, to devices designed to measure the volume of liquid or gas in a tank in a noninvasive manner.

BACKGROUND OF THE INVENTION

The use of indicators to measure the volume of liquid or gas in tanks or containers is well known. Such indicators are typically of the invasive type, in that they are constructed to measure the volume or level of liquid or pressure of a gas in a tank or container through the use of one or more members or devices that reside within the tank itself or that are in liquid or gas communication with the inside liquid- or gas-containing chamber of the tank. Such invasive-types of liquid or gas measuring devices can include one or more members that are also disposed outside of the tank. Invasive measuring devices are adequate for use in certain applications where the tank is either not covered or enclosed, or is covered and pressurized or not pressurized.

However, even in these types of containers the use of invasive measuring devices may not be the most suitable method for determining the volume content of the liquid or gas disposed therein. For example, the placement of an invasive measuring device within the volume of a container in certain applications may carry with it the risk of possibly contaminating the liquid or gas disposed there, e.g., when the liquid or gas is of a high purity. Further, exposing one or more element of a measuring device to the liquid or gas being measured may carry with it the risk that such exposed elements may become damaged, e.g., in the case where the liquid or gas is corrosive or the like. Additionally, the use of such an invasive measuring device also requires a breach of the container structural wall, which can introduce a source for a possible leak path of the liquid or gas from within the container. The introduction of such a leak path may not be desired in certain applications where an unintended release or the liquid or gas could present a health, safety or environmental risk.

Additionally, there are certain types of specialized liquid or gas handling containers that are pressurized for the purpose of performing a particular function. An example of this type of container is a hydraulic surge suppressor that comprises a pressurized diaphragm disposed therein for the purpose of accommodating a pressure surge or hydraulic transient in the fluid line that it is attached to. In such an example application, it is intended that the gas within the diaphragm be maintained under substantial precharge pressure for the purpose of attenuating any fluid surge within the fluid line. Because the pressure vessel comprises an elastomeric bladder disposed therein, the use of conventional invasive-types of volume measurement devices can present a challenge (due to the combined contents of a liquid volume and a gas-filled elastomeric bladder), and can interfere with the intended operation of the device. Further, because such surge suppressors are operated at elevated pressures, it is desired that the container not include any perforations or holes through the structural wall.

In addition to the above-noted issues related to measuring liquid or gas volumes in a container by invasive devices or methods, it is desired for certain liquid and gas volume measurement applications that the measuring device and/or the instrumentation used with the same be sufficiently portable to permit the unhindered measurement of a number of tanks or containers at one or more locations. In order to provide such flexibility using an invasive method of volume measurement, each tank or container being measured would have to in advance be constructed to include the invasive measurement device, which adds both to the initial cost of constructing the container and the later costs of servicing and maintaining proper operation of the measurement device.

It is, therefore, desired that a device and method for using the same be provided that is capable of obtaining an accurate measurement of liquid or gas volume within a container in a non-invasive manner. It is desired that such device be capable of providing such volume measurement in liquid or gas containers that may or may not comprise a pressurized diaphragm or other type of pressurized member therein. It is further desired that such noninvasive volume measurement device be somewhat portable so that it can be used to measure the volume in more than one liquid container in a manner that is both time and cost effective.

SUMMARY OF THE INVENTION

Acoustic volume indicators of this invention make use of a noninvasive measuring technique for determining the liquid or gas volume within a container. Acoustic volume indicators of this invention comprise the following components (a) a resonating means disposed along an outside wall surface of the container to impact and vibrate the container wall; (b) a resonating detection means disposed along the container outside wall surface to receive vibration data from the container wall; (c) a detection and processing means for converting the vibration data to frequency information and comparing the frequency to characteristic frequency vs. volume data of the container to obtain the measured volume; and (d) an indicator means for providing a desired visual and/or audio indication of the measured volume.

The resonating means can be provided in mechanical or electromechanical form, e.g., can be in the form of an impactor that can be activated to strike the outside wall surface of the container. The resonating detection means can be in the form of a detector designed to respond to vibration signals provided from the tank wall.

The detection and processing means can be provided in the form of a processor configured to receive vibration data provided from the detection means, convert the vibration data into frequency information, e.g., by process of Fast Fourier Transform (FFT) or the like, and compare the frequency information to the characteristic container frequency vs. volume data to determine the measured liquid or gas volume. The frequency detection and processing means provides an output signal to an indicator device to provide an indication of the measured container volume.

In one invention embodiment, the processor comprises a microprocessor device disposed within a housing comprising a number of lights that are each configured to represent a volume level of the container. The microprocessor is configured to receive the vibration data from the detection means, and provide an output signal to one of the lights indicative of the measured container gas or liquid volume. In this embodiment, the microprocessor is calibrated to provide such output using the characteristic frequency vs. volume data for the container.

In another invention embodiment, the processor comprises a computer that uses a computer program to convert the vibration data from the detection means, convert it to frequency information, analyze the frequency information to identify a peak frequency, and compare the peak frequency to the characteristic frequency vs. volume data for the container to determine the container liquid or gas volume. The computer and computer program provides an output to an indicator means in the form of an electronic video monitor that displays the measured liquid or gas volume.

BRIEF DESCRIPTION OF THE DRAWINGS

This invention may be more clearly understood with reference to the following detailed description, and by reference to the following drawings in which:

FIG. 6 is a schematic diagram illustrating another example embodiment acoustic volume indicator of this invention.

DETAILED DESCRIPTION OF THE INVENTION

Acoustic volume indicators, constructed according to principles of this invention, are constructed for the purpose of enabling an accurate indication of liquid or gas volume within a container in a non-invasive manner, and operate on the principle that as the volume of liquid or gas within the container changes, so too does the natural resonating frequency of the container wall or shell. For example, with respect to measuring liquid, as the liquid volume within a container increases, the natural resonating frequency of the container wall decreases. With respect to measuring pressurized gas, as the gas pressure within a container increases, so too does the natural resonating frequency of the container wall.

Acoustic volume indicators of this invention generally comprise a means for implementing or causing a liquid or gas container to resonate, a means for detecting the resonation signal from the container, a means for converting the detected resonation signal to a liquid or gas level or volume within the container, and a means for displaying the measured liquid or gas level or volume, and/or providing an audio and/or visual output signal in the event that the measured liquid or gas level or volume is different than a predetermined level.

Figure 1:
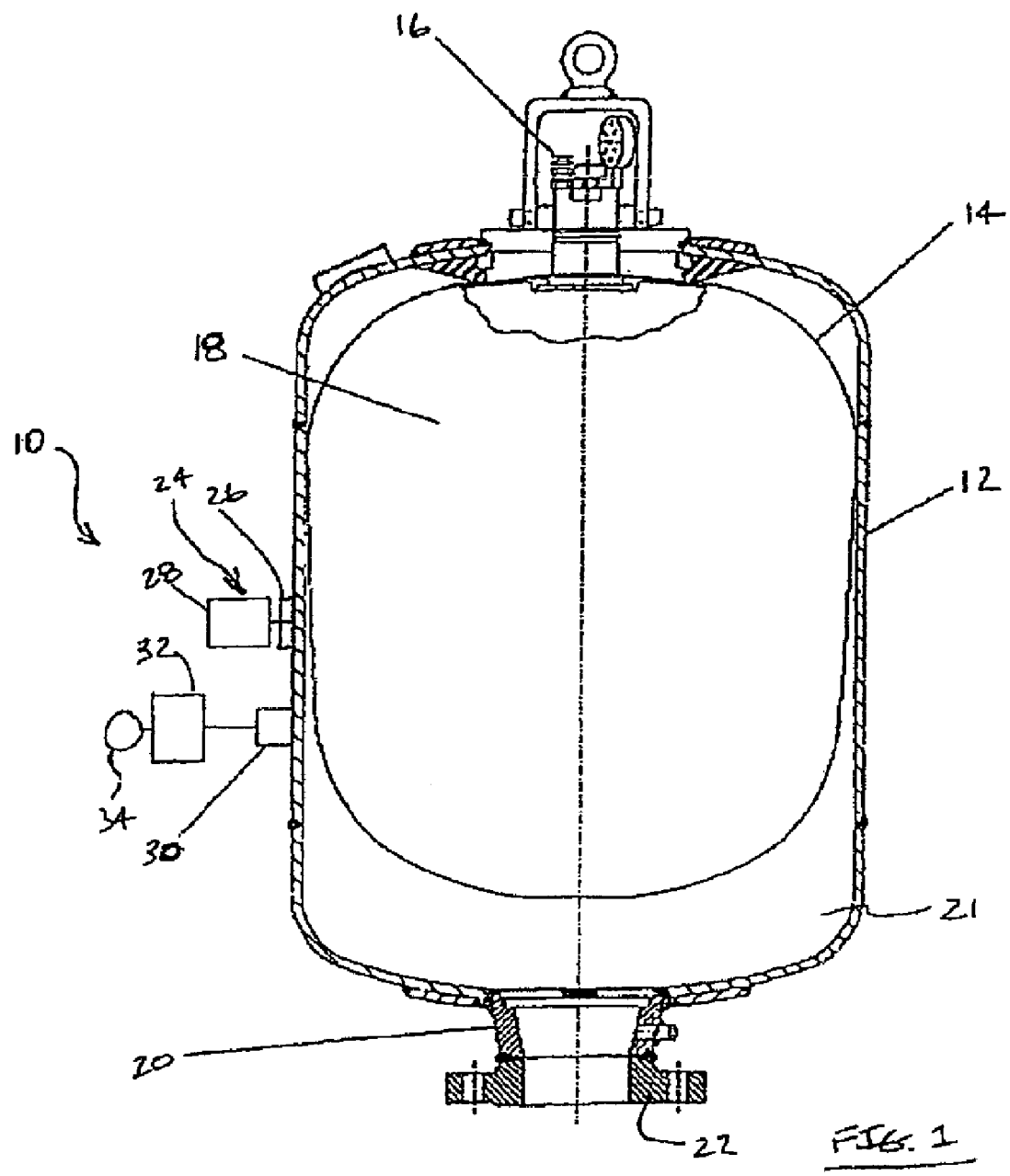
FIG. 1 is a schematic cross-sectional side elevation illustrating an acoustic volume indicator, constructed according to an embodiment of this invention, as used with a liquid volume container.

FIG. 1 is a schematic diagram illustrating an acoustic volume indicator 10 according to a first embodiment of this invention. As shown in FIG. 1, the indicator 10 is used to measure the liquid volume within a tank or container 12 that comprises an internal bladder 14 disposed therein. An example of such a tank is one used to suppress hydraulic surge that comprises an internal pressurized bladder or diaphragm for the purpose of accommodating a pressure surge or hydraulic transient in a fluid line that is connected thereto.

In such tank embodiment, the internal bladder 14 is disposed within an internal chamber of the tank, and services to separate liquid that enters and that is contained within the tank from compressed gas, in this case, air. The air is supplied from a pressurized source (not shown) through a valve 16, which is preferably molded to the bladder 14, and into a chamber 18 within the bladder 14. The valve 16 is positioned at one end of the tank. The bladder is sized and shaped to fit within the tank and to fully occupy the diameter of the tank when placed into a precharged pressurized condition. The tank includes a fluid inlet 20 at another end that is in fluid flow communication with the tank internal chamber 21. A flange or other conventional fluid transport coupling 22 is connected to the fluid inlet 20 to direct liquid to the tank from an external source (not shown).

Although the indicator 10 of this invention has been described and illustrated as being used to measure a liquid volume of a particular type of liquid container, it is to be understood that indicators of this invention can be used with a wide variety of liquid containers other than that specifically described and illustrated. Additionally, indicators of this invention can be used to not only measure the volume of liquid within a container, but can be used to measure a volume of gas within a container. The acoustic volume indicator of this invention can function to measure the volume of gas within a container when the gas is either in a gas or a liquid state, e.g., when the gas is placed under such a pressure within the container to cause it to be compressed or pressurized to a liquid state. Thus, as used herein, the term liquid is understood to refer to the group of materials that are in a liquid state at ambient pressure, and to the group of gases that can be placed into a liquid state at elevated pressures. Additionally, however, it is to be understood that the indicator of this invention can be used to measure the volume of a gas present in a gaseous state within a container.

The acoustic volume indicator comprises a number of different elements, wherein all or some of the elements can be portable or fixed relative to the tank being measured. For example, the acoustic volume indicator 10 can be fixedly mounted to the tank, or can be provided as portable unit, i.e., having one or more components packaged as a hand-held portable unit. In either embodiment, the indicator 10 is generally configured for fixed or removable placement adjacent an outside wall surface of the tank for making contact therewith.

The indicator 10 comprises means for causing a wall of the tank 12 to resonate or initiate tank resonation. In this indicator embodiment, such resonating means 24 is in the form of a device that can be positioned adjacent an outside wall surface of the tank, and that is configured having a member that physically contacts, strikes or otherwise impacts the tank outside wall surface. Alternatively, instead of using a mechanical device, the resonating means can be in the form of an electromechanical device capable or providing the desired vibrating motion without mechanically contacting or striking the tank wall.

In an example embodiment, where the resonating means is embodied as a mechanical device, it is provided in the form of an impact device or contactor 26 that includes a contacting portion or head that is connected to a suitable actuation mechanism. The contacting portion or head can be configured and/or formed from materials that will operate to produce a desired resonation of the tank wall when placed into contact therewith. The contacting portion or head can be provided in the form of a spherical ball, any shape having a radiused or curved surface, or any shape having a flat surface to provide the desired wall resonation upon making contact therewith. Additionally, the contacting portion or head can be formed from such materials as felt, rubber or the like that operate to cause the tank to resonate at its natural frequency when struck thereby. In an example embodiment, the contacting portion or head can be attached to a desired actuation mechanism or actuator by a shaft. The shaft can be formed from any type of structural material, e.g., metallic or nonmetallic, suitable for providing a desired connection between the contacting portion and the actuator. In an example embodiment, the shaft is formed from a polymeric nonmetallic material.

While particular types of contactors have been described, it is to be understood that other types of mechanical devices adapted to strike the tank wall in some way can be used. For example, a coil-type plunger, or an electric solenoid plunger or other device can be used to lightly impact the outside wall surface of the tank being measured. In one example embodiment, the contactor can be manually actuated and comprises a contacting portion of head mounted to a shaft, a handle attached to the shaft, a hinge pin interposed between the contacting portion, and a spring to provide the desired biasing of the contactor. In an example embodiment, the contactor 26 is spring loaded by a compression spring with a trigger to enable consistency in the amount of energy that is impacted to the tank shell. In such example embodiment, the contactor components comprising the contacting portion or impact head, the shaft connected thereto, and the compression spring are all disposed within a common housing. The resonating means can be a portable device or can be removably or fixedly attached to an outside wall surface of the tank.

In an example embodiment, the impact energy provided by the contactor is on the order of approximately 0.003 ft-lbs. It is to be understood that this number is representative of only one example, is provided for purposes or reference, and is not intended to be limiting. Ultimately, the impact energy that is provided by the contactor is an amount that is suitable for achieving the desired effect for the particular tank or container. The resonating means can include means for adjusting the impact energy provided therefrom. As better described below, the resonating means 24 can be activated by a controller to strike the tank in response to receiving a resonation initiating signal.

The indicator includes means for sensing tank resonation, or sensing means, caused by the resonating means 24. The sensing means 30 can be removably or fixedly attached to the outside wall surface of the tank or container 12. The sensing means 30 can be any type of device that is capable of picking up or detecting the vibration motion of the tank wall caused by the resonating means, converting the vibration motion to an electric response signal for further processing and/or evaluation. In an example embodiment, the sensing means 30 is provided in the form of an accelerometer that is designed to detect for processing the vibration signal/signature of the tank generated by the resonating means. The sensing means is designed to respond to an increased amplitude of signals sensed at the resonant frequency of the tank. In another example embodiment, the sensing means is provided in the form of a microphone/transducer vibration pick-up device.

In an example embodiment, it is desired that the sensing means 30 be positioned relatively close to the placement position of the resonating means. In a preferred embodiment, the sensing means is positioned on the tank outside wall surface a distance of from about 2 to 6 inches away from the impact point of the resonating means. In an example embodiment, it is desired that the sensing means be positioned within this distance as such relatively closely placement operates to reduce the required impact energy that is needed to adequately vibrate the tank wall and trigger the acoustic volume indicator.

The sensing means 30 provides the response signals to a detector and signal processor 32, which provides filtering, FFT or other signal processing functions, and which compares the processed response signal to preprogrammed specific frequency vs. volume characteristics of the tank. The signal processor 32 is designed for easy data input and is capable of storing hundreds of frequency vs. volume data, i.e., acoustic signatures, for all different tank shapes, sizes and pressures.

In an example embodiment, the detector and signal processor 32 are configured to condition and/or convert the response signal obtained from sensing means 30 to a form usable by an output device or devices capable of providing an indication of measured volume. In this example, the signal processor 32, after receiving and processing the input signal and comparing it to the frequency vs. volume data for the measured tank, produces an output signal to a indicator means 34, e.g., a visual indicator in the form of a gage or other suitable visual display medium, thereby providing the user with a visual indication of the measured tank volume. If the response signal processed by the signal processor indicates that the quantity of liquid within the tank is outside of a desired range, the indicator means 34 can be configured to respond accordingly, e.g., by providing a visual and/or audible alarm indication. For example, the signal processor 32 can be preprogrammed to provide an output signal to a green light of the indicator means if the measured frequency of the tank is between a certain range (indicating a proper liquid volume in the tank), and provide an output signal to a red light of the indicator means if the measured frequency is outside of a certain range (indicating an improper volume in the tank).

Although the use of a particular type of indicating means 34 has been described and illustrated, it is to be understood that the system can be adapted to provide a variety of different visual and/or audio indicators of measured volume. For example, rather than a gage, an indication of the measured volume can be provided on a screen of an electronic video display device, such as a computer monitor or the like. If desired, the measured volume can be provided in graphical form on such type of electrical display device for easy viewing and monitoring, and for charting if so desired. Additionally, the indicating means 34 can be configured to provide an audible signal, independent of or together with a visual indication, as a warning signal in the event that a certain predetermined measured volume is not detected. This audible signal could be useful in the situation where the measured volume is above or below a predetermined danger set point, thus representing a warning alarm. Additionally, the indicating means can be provided at a location adjacent the tank being measured or at a position remote from the tank, such as within a control room or the like.

In another embodiment, the acoustic volume indicator of this invention comprises a resonating means 26 that is designed to generate a sweep frequency vibration within the tank, instead of producing a momentary impact impulse. In an example embodiment, the resonating means is in the form of an electromechanical vibrator 28 that includes an impactor 26 configured to impact the wall of the tank 12 with a sweep frequency signal. The sweep frequency signal from the vibrator 28 is designed to cover a range of frequencies, which includes resonant frequencies between those resulting from impacting a full tank to those resulting from impacting an empty tank. The vibration provided by the vibrator 28 is transmitted through the wall of tank 12 to the contents contained therein. Like the previous indicator embodiment discussed above, the resonating means of this indicator embodiment can be activated by a controller or other type of user operated or automatically operated initiating or actuating device.

A sensing means 30 is attached to an outside wall surface of the tank and is provided in the form of those sensing means discussed above for the previous embodiment indicator. The sensing means detects and for further processing the vibration signature of the tank as generated by the resonating means 26. The sensing means 30 is designed to sense an increased amplitude, when a resonant frequency occurs in the tank, and transmit this response signal to the signal processor. If desired, a filter can be used to treat the response signal prior to or during further signal processing by the signal processor 32. The signal processor 32 is designed to receive the response signal from the sensing means or accelerometer 30. The filter is deigned to limit the signal processing to a frequency range representative of frequencies varying between those indicating a full tank to those indicating an empty tank. There will be a sharply increased amplitude signal sensed at the accelerometer 30 at each resonant frequency representing the current volume within the tank 12.

The signal processor 32 is designed to operate in the manner described above for the previous indicator embodiment, i.e., to analyze and convert the response signal provided by the sensing means and convert the time domain resonation signal to a frequency domain signal. The frequency domain signal is then compared to preprogrammed frequency vs. volume data that is characteristic of the tank being measured. Again, it is desired that the signal processor 32 be designed for easy data input, and be capable of storing hundreds of frequency vs. volume data, i.e., acoustic signatures, for all different tank shapes, sizes and pressures.

Like the previously described indicator embodiment, the detector and signal processor 32 of this other embodiment indicator is also configured to convert the response signal obtained from the sensing means 30 to a form usable by an output device or indicating means 34, e.g., a visual gage or other visual and/or audible indicator, to indicate the measured volume within the tank.

Again, as described for the earlier embodiment indicator, this other indicator embodiment can be configured to provide a variety of output signals. For example, rather that an output signal to an indicator gauge, the system can be adapted to provide an output signal to a visual display device such as an electronic video monitor to provide a visual indication of the measured volume, and can be configured to provide a visual and/or audible alarm signal in the event that the measured volume in the tank is above or below an alarm set point. Additionally, the indicator output can be provided to a location adjacent the tank or a location remote from the tank, e.g., to a control room if so required.

Although the indicating components described above, used for forming the acoustic indicating device of this invention, have been illustrated in FIG. 1 in a particular manner, it is to be understood that this has been done for purposes of reference. If desired, the members can be grouped or combined differently than that described and illustrated. Additionally, the indicating components have been illustrated having a particular scale for purposes of easily identifying the same for reference, which scale may or may not be accurate or to scale relative to the invention as practiced.

In an example embodiment, acoustic volume indicators of this invention are packaged in the form of a small electronic device provided in one or more housings that are capable of either being portable, e.g., hand held, or removably or fixedly attached to the tank under test. In such embodiment, the indicator has a portable power supply, e.g., is battery powered making use of commonly available battery sizes. The indicator comprises one or more housing that is made from a suitable sturdy material, and is preferably of a weatherproof design. It is desired that the indicator be capable of exposure to ambient temperatures of from minus 20° F. to 120° F. with exposure to direct sunlight, and be designed for operation in ambient temperatures of from 30° F. to 110° F.

Figure 2:
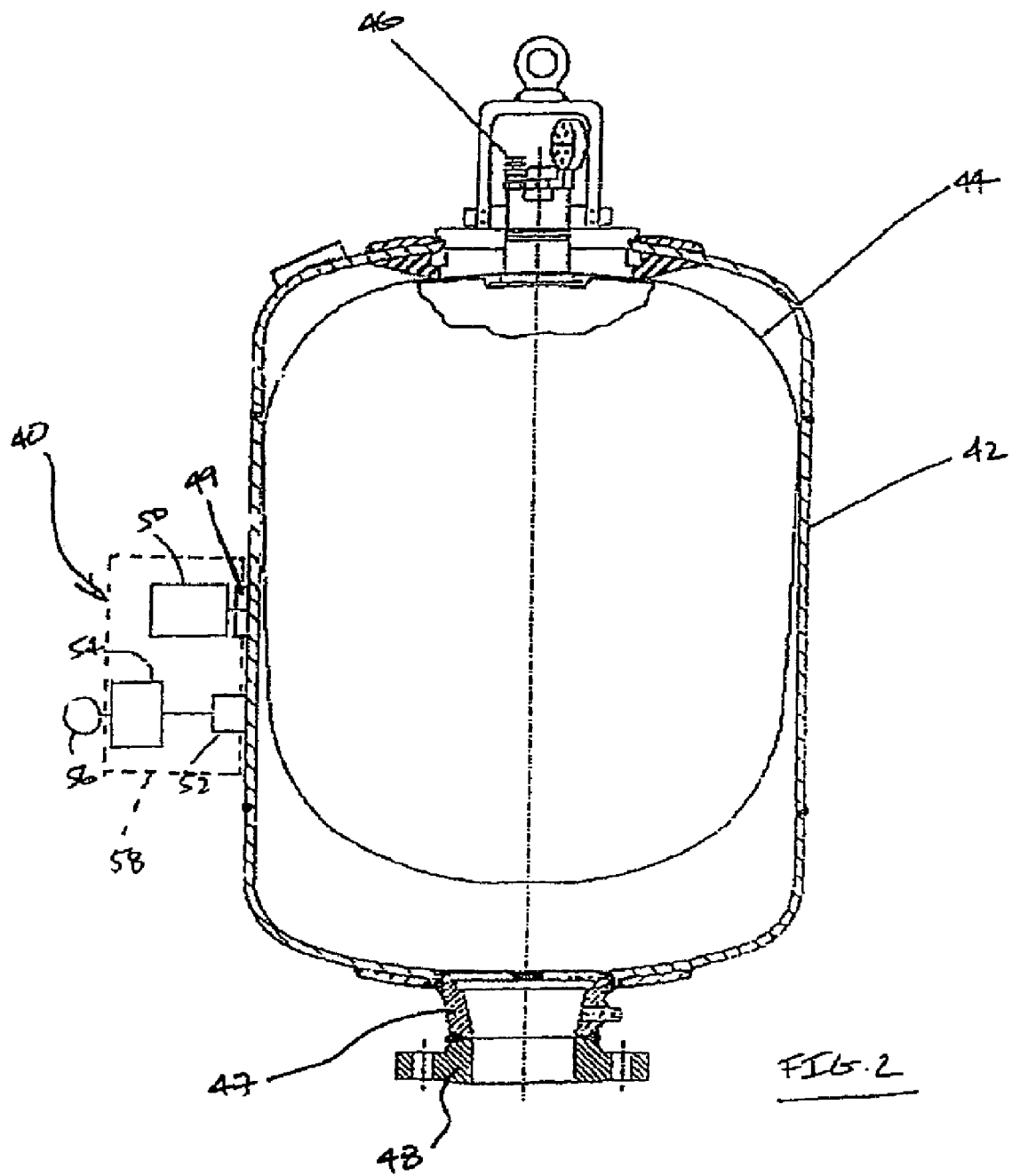
FIG. 2 is a schematic cross-sectional side elevation illustrating an acoustic volume indicator, constructed according to another embodiment of this invention.

FIG. 2 is a schematic diagram illustrating an acoustic volume indicator 40 constructed according to an embodiment of the invention as used with the same type of tank or container 42 described above for the indicator embodiment of FIG. 1. The tank 42 again comprising an internal gas pressurized bladder or diaphragm 44 having a gas charge valve 46 positioned through one end of the tank. The tank 42 includes a fluid inlet 47 at an opposite end that is configured to accommodate attachment with a fluid transport coupling 48.

This indicator 40 in this particular embodiment is illustrated as having its components, i.e., the resonating means 49 and 50, the sensor means 52, the detector and processing means 54, and indicating means 56 disposed or container within a common housing 58. The housing can contain the indicator components in such a manner as to promote portability of the indicator, or can contain the indicator components in such a manner as to provide a fixed indicator, depending on the particular application and use requirements.

Acoustic volume indicators of this invention comprise a number of different electrical circuits configured to operate the above-described different indicator components. In an example embodiment, the indicator comprises the following electrical circuits: (1) a power supply and regulation circuit; (2) a user control circuit; (3) a resonation excitation circuit; (4) a resonation detection circuit; (5) a resonation signal conditioning circuit; (6) a frequency detection circuit; and (7) a user display circuit.

The power supply and regulation circuit is designed to provide necessary voltage and current required for operation of the different indicator components, such as the resonating means, the sensing means, and the processing means. The power supply and regulation circuit is also used to provide necessary power to the other identified electrical circuits of the indicator.

In an example embodiment, user control over acoustic volume indicators of this invention is provided in the form of a power switch and a keypad. The power switch allows a user to turn on and turn off the indicator, so that energy can be conserved when the indicator is not in use. The user control circuit provides input from the keypad to a microprocessor in the indicator, so that the microprocessor can send power to the resonation excitation circuit. The keypad may also be used to reconfigure and/or tune the indicator to provide system flexibility, thereby enabling acoustic volume indication use across a wide range of volume measurement applications.

The resonation excitation circuit is used to activate the indicator resonating means to cause the tank under test to resonate. In an example embodiment, the resonation excitation circuit is implemented with a solenoid that when excited causes an impact to be made with the tank under test to initiate resonation. The resonation excitation circuit does not have to be limited to such a device, as it could be further implemented by nonphysical mechanical means such as by an acoustic coupling. Additional means for initiating tank resonation include magnetic, nuclear, strong or weak forces. Alternatively, this circuit could be removed from the indicator and provided by an external means for the purpose of exciting the tank wall into resonation.

The resonation detection circuit is used to convert the natural physical resonation of the tank wall, taken by the sensing means, into a form that can be processed for the detection of information content from the signal. In an example embodiment, the resonation detection circuit is provided by using an accelerometer that when the tank wall is excited creates an electrical signal that is proportional in frequency and amplitude to the mechanical resonance of the tank wall under test. The resonation detection circuit does not have to be limited to such a device, as it could be further implemented by non-acoustical mechanical means such as by physical coupling. Additionally, magnetic, nuclear, strong or weak forces could be used to implement tank resonation detection.

The resonation signal conditioning circuit is designed to condition the detection signal by amplification so that the following frequency detection circuit can operate properly. The frequency detection circuit is designed to convert the time domain resonation signal into a frequency domain signal. In an example embodiment, this conversion is done with a microprocessor-based device in conjunction with an analog-to-digital converter and FFT or Discrete Fourier Transform (DFT) algorithms. The output of the algorithm can be displayed on an electronic video display, e.g., on a liquid crystal display (LCD), and transmitted from the microprocessor, e.g., out of a serial port, USB port or the like, for remote use.

The user display circuit is designed to provide a user with a visual indication of, but not limited to, test progress, system power condition, and measured tank volume based on detected resonation of the tank under test. The current implementation is done with an electronic video display device but is not limited to such as device.

Acoustic volume indicators of this invention are placed into volume indication operation by the user's act of engaging the user control noted above, e.g., by pressing one or more buttons of a user interface such as a keypad. This act activates the resonation excitation circuit, thereby causing the resonating means to initiate resonation of the tank wall. In the first embodiment indicator, this act energizes the solenoid 28 to activate the contactor or plunger 26 to impact the outside wall surface of the tank. In the other embodiment indicator, this act energizes the electromechanical vibrator 28 to activate the impactor 26 to cause the wall surface of the tank to resonate.

The other circuits of the indicator are also activated, and the resonation detection circuit operates with the sensing means or accelerometer 30 to record the response to an impact signal and transfer the response data to the detector and signal processor 32 for processing such as FFT or DFT to determine the natural or resonant frequency of the tank 12. This frequency information is then compared by the signal processor 32 with the pre-programmed characteristic frequency vs. volume data for the tank via the frequency detection circuit, and an output signal is provided to a desired user display or indicator, e.g., a video monitor, gage or the like, to provide a visual indication of the measured tank volume As noted above, acoustic volume indicators of this invention are not limited in application to the noninvasive detection and measurement of liquids within containers having gas-filled bladders disposed therein, but can also be used to non-invasively measure the volume of liquids within containers that do not have gas-filled bladders. Further, acoustic volume indicators of this invention can also be used for noninvasively measuring the volume of gases disposed within pressurized tanks or containers in applications where the gas is pressured within the container and is in either a gas or liquid phase.

Figure 3:
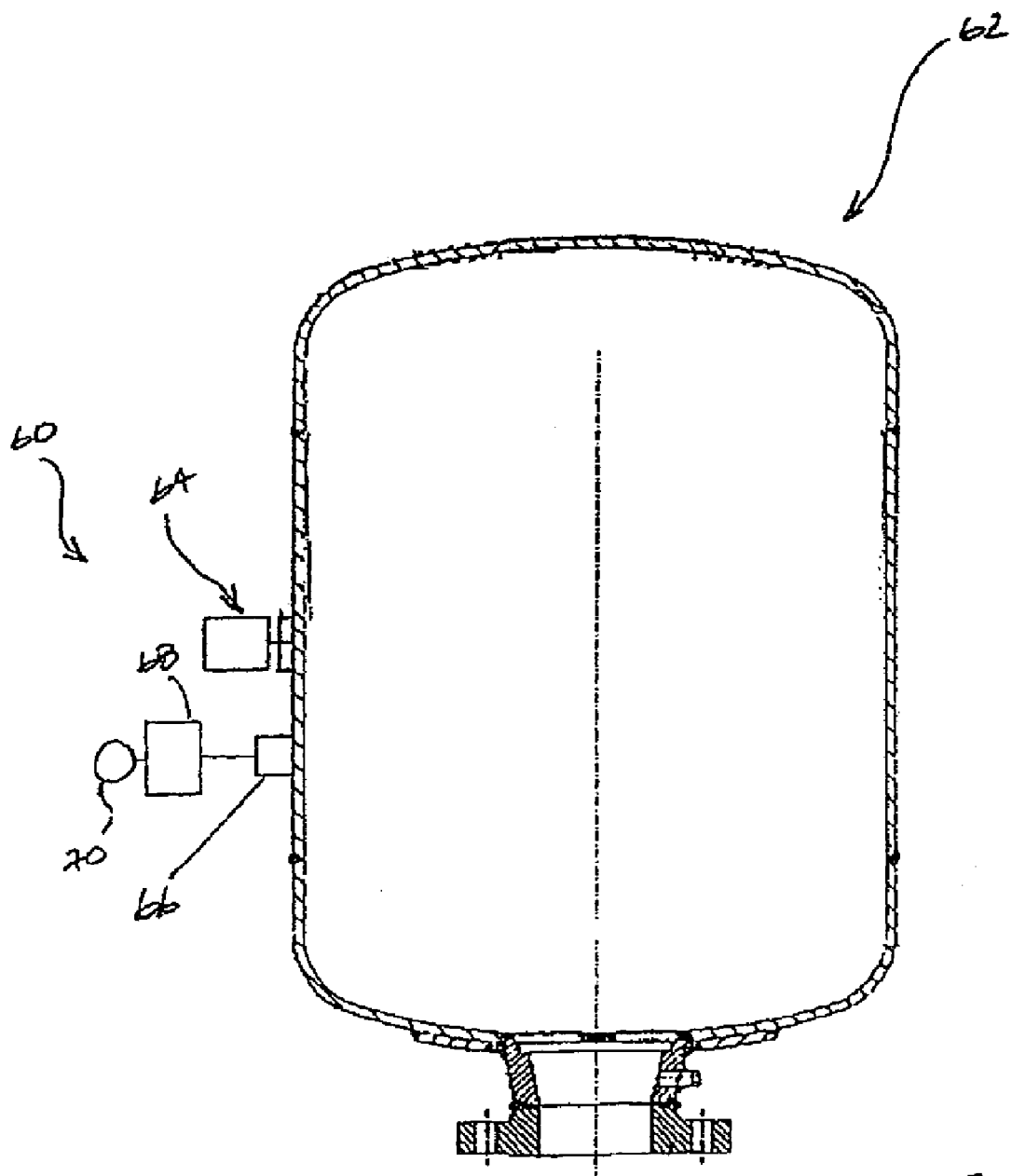
FIG. 3 is a schematic cross-sectional side elevation illustrating an acoustic volume indicator, constructed according to another embodiment of this invention, as used with a liquid or gas container.

FIG. 3 is a schematic diagram illustrating an acoustic volume indicator 60, constructed according to an embodiment of the invention, as used either with a container 62 that is configured to accommodate a volume of liquid therein (without a gas-filled bladder), or that is configured to accommodate a volume of pressurized gas therein. In both measurement applications, the indicator is configured comprising the same general components described above; namely, the resonating means 64, the resonating detecting or sensing means 66, the detector and signal processor 68, and the visual indicator means 70.

The indicator 60, when configured for measuring a liquid volume in the container 62, is configured in the same manner as described above and operates on the principle that as the liquid volume in the container increases, the natural resonating frequency of the tank wall decreases. Accordingly, the microprocessor used in this application is loaded to contain the characteristic frequency vs. liquid volume data for this particular tank.

It has been discovered that the relationship between gas pressure or volume and the natural resonating frequency of the gas container wall is the opposite of that of liquid. Namely, as gas pressure or volume within the container increases, the natural resonating frequency of the gas container wall increases. Thus, when configured for measuring a gas volume in the container 62, the indicator 60 is configured in generally the same manner as described above for use in liquid volume measurement, but with the exception that the microprocessor is loaded with the characteristic frequency vs. gas volume data for this particular tank that reflects this trend.

Figure 4:
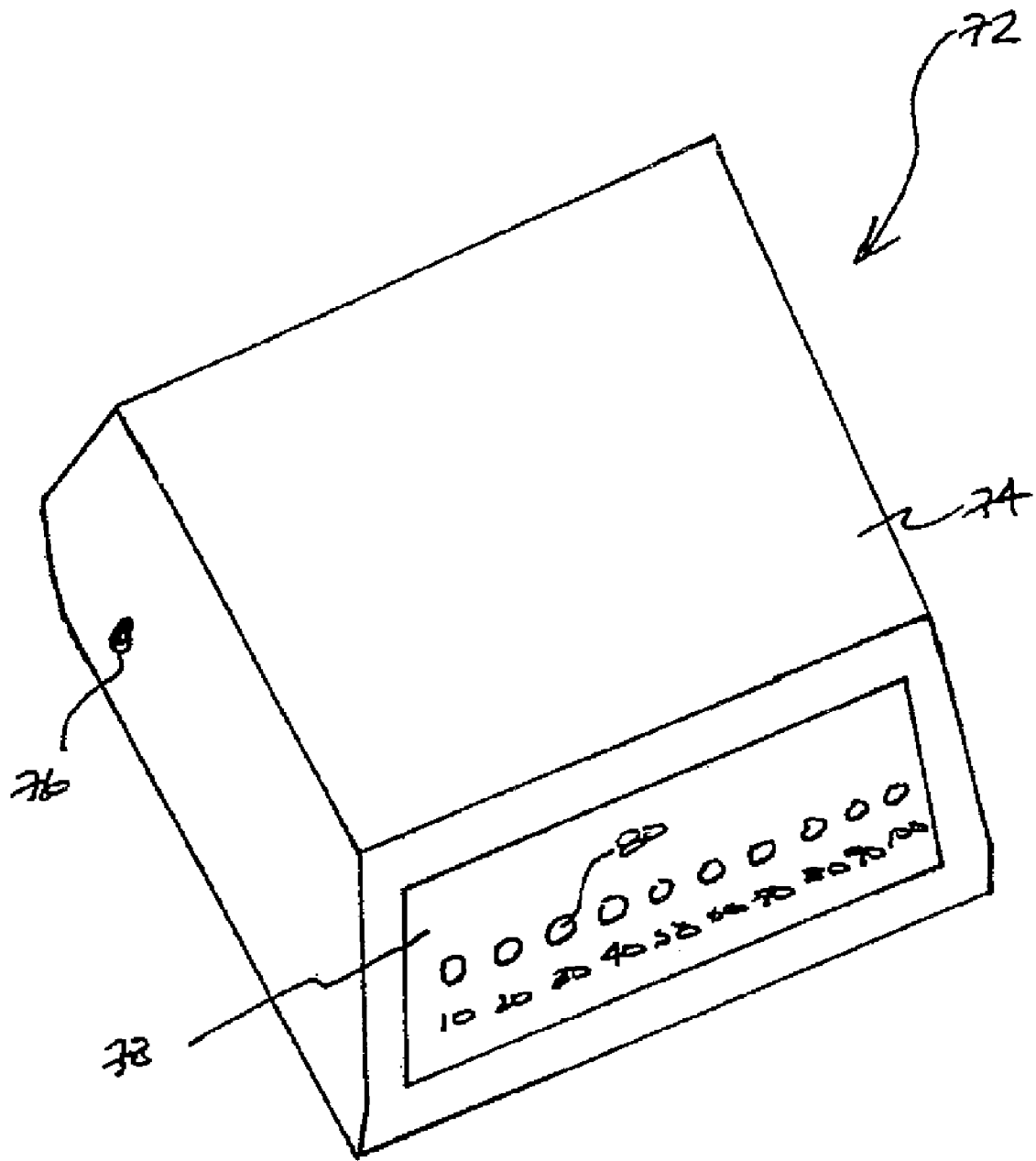
FIG. 4 is a schematic diagram illustrating an example embodiment detector and processor as used with acoustic volume indicators of this invention.

Acoustic volume indicators of this invention can be configured using different types of detectors and signal processors, depending on the particular use application and user need. FIG. 4 illustrates an example embodiment of a detector and signal processor 72 that generally comprises a housing 74, a portable power source disposed within the housing, or a port to access a source of power, and an input port 76 for receiving the response signal from the resonating sensor means. The processor is generally configured to receive a response signal from the resonating sensor means, and to process the response signal in a manner that produces a visual volume measurement indication. The processor includes a visual display 78 that comprises a number of light sources 80 disposed therein. The processor is configured to receive the response signal and produce an output signal to activate one or more of the light sources 80. The processor is calibrated so that each light source 80 represents a different measured volume. A detector and processor configured in this manner and suitable for use in such volume measurement application include those disclosed in U.S. Pat. Nos. 5,388,496 and 5,396,827, which are each incorporated herein by reference.

Generally speaking, the detector and signal processor in such embodiment is configured with the light sources calibrated to a specific liquid or gas volume of the tank or container being measured, and is configured to receive the response signal and process it to operate a respective light source indicative of the volume within the tank according to the calibration parameter. Accordingly, such processor must be calibrated for each different type of container that it is used to measure.

The processor 72 includes one or more electrical circuits that convert the incoming response signal into electrical signals that can be amplified by an amplifier, that can be filtered in a frequency response amplifier, that may be detected by a zero crossing detector, and that may be analyzed by a microprocessor that is configured to operate the one or more light sources, e.g., LEDs. The microprocessor determines the resonating frequency of the incoming response signal, computes the nearest container gas or liquid volume, and operates the corresponding light source in the display. For example, for a 100 gallon capacity container, the processor may include 10 light sources 80 in its display that each designate a different incremental volume of the container, e.g., 10 gallon increments where the first light source indicates a 10 gallon volume measurement and the last light source indicates a 100 gallon volume measurement. Alternatively, the microprocessor can be configured to operate more than one light source in the display to provide a visual indication of the cumulative measured volume, e.g., for the above example, if an 80 gallon measurement was identified then the processor would illuminate the first 8 light sources. It is to be understood other variations of processor volume display can be developed within the scope of this invention according to the particular application and/or user need.

Figure 5:
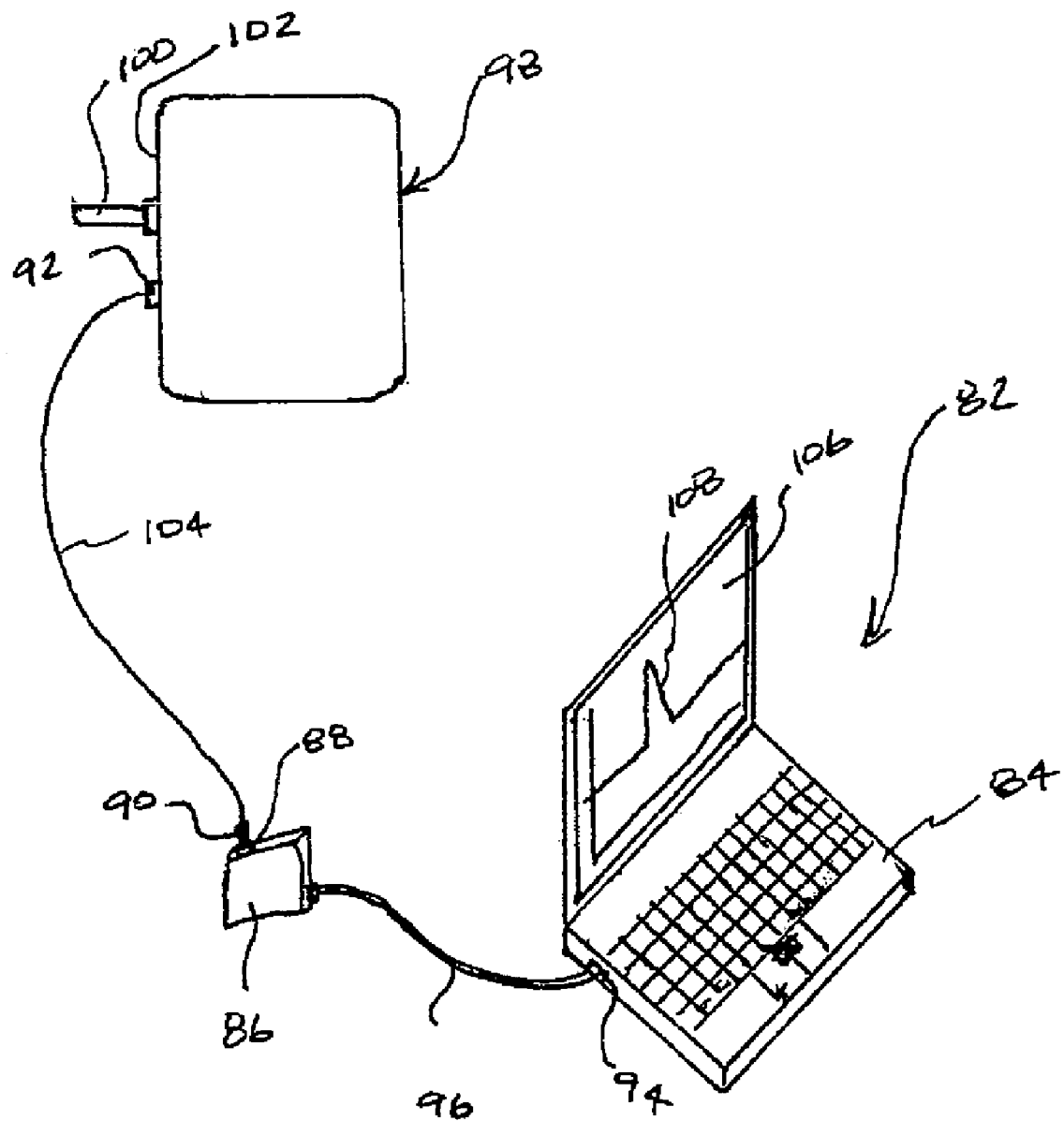
FIG. 5 is a schematic diagram illustrating another example embodiment of the detector and processor as used with acoustic volume indicators of this invention.

FIG. 5 illustrates another example embodiment detector and processor 82, used with acoustic volume indicators of this invention, provided in the form of a computer software program that is implemented using computer 84, e.g., provided in the form of a laptop, desktop, tablet, or pocket PC. In an example embodiment, the software program can be one designed to perform a waveform or spectrum analysis. In an example embodiment, the software program is configured to be run on a computer using a Windows-based operating system. In this particular embodiment, the waveform analyzer software program is developed to decipher an incoming response signal from the resonating sensor means, convert the response signal to a frequency spectrum, analyze the frequency spectrum, and capture the dominant natural vibration frequency or frequency peak.

The program has also been specially developed to capture only that portion of the response signal providing relevant waveform data for isolating and analyzing the resulting frequency of the resonating container wall. Additionally, the program can be configured to filter out any unwanted excitation or other noise that can interfere with the further processing and analysis of the waveform signal. Once the frequency peak is captured, the program is configured to launch it into a data file where it is compared against a calibration curve to determine an indication of the volume in the tank.

A sound card 86 is used in conjunction with the software program and can be provided as a device that is mounted within or that is external of the computer 84. In an example embodiment, an external sound card 86 is used and includes a microphone inlet port 88 that permits attachment with an outlet plug 90 from the resonating sensor means 92, e.g., in the form of an accelerometer or a microphone/transducer device. In an example embodiment, the external sound card that is used is one that is readily available. In an example embodiment, the microphone/transducer or accelerometer device is one that is also readily available. The external sound card is configured to amplify the vibration signal transmitted from the sensor means, and has an adjustable amplification level. The external sound card 86 is connected to the computer 84 by cable 96 via a USB port 94 that both provides power to the sound card and facilitates transfer of the amplified vibration signal to the computer for subsequent processing by the computer software.

The computer software is configured to access characteristic frequency vs. volume data for a particular container or tank 98 to be measured that can be provided for example in the form of a spreadsheet or in a form of a text file. The frequency vs. volume data can either be saved on the computer's hard drive or can be provided in the form of a disk or diskette and loaded on to the computer at the appropriate time. In an example embodiment, the characteristic frequency vs. volume data for a particular container can be provided in the form spreadsheet formatted as an Excel document and provided in the form of a disk.

Accordingly, the processor 82 functions in the following manner. If not already installed, a user loads the spectrum analyzer computer software onto their computer 84, loads the container characteristic frequency vs. volume data onto their computer, connects and installs the external sound card 86 to the computer, attaches the resonating means 100 and resonating sensor means 92 to the outside wall surface 102 of the container 98 to be measured in the manner described above, and connects the output 104 from the resonating sensor means 92 to the sound card 86. The user then enters the spectrum analyzer software program on the computer or handheld device and accesses the relevant menu as displayed on the video monitor 106 to confirm that the characteristic frequency vs. volume data is loaded. The user places the program into a "run ready" mode that, in an example embodiment, provides an image of an oscilloscope on the video monitor 106 of the computer or handheld device. The user then places the program into the "run" mode and activates the resonating device to impact the tank 98. A resulting frequency peak 108 is displayed on the on the video monitor 106 and the user can then launch the frequency peak into the characteristic frequency vs. volume data, and the program will then determine and display the measured volume. Alternatively, the program can automatically launch the frequency peak and display the measured volume upon initially determining the frequency peak.

Although the software based waveform analysis program described above was presented as being used with a computer 84, e.g., in the form of a laptop or desktop computer, it is to be understood that the implementation of such waveform analysis program should not be limited to such computers. For example, the waveform analysis program, useful with acoustic volume indicators of this invention, can also be implemented through the use of a handheld electronic device such as a handheld PC or the like in the form of a software program or as a hardware component installed in the handheld device, e.g., installed in the form of one or more integrated circuits or chips.

Acoustic volume indicators of this invention can be provided as a portable device, useful in such applications as taking field volume or gas measurements of a number of different containers in one or more locations. Alternatively, the acoustic volume indicators of this invention can be configured having one or more component, e.g., the resonating means and/or the resonating sensing means, that remains fixed to the tank or container, for taking repeated volume measurements of that same tank over a period of time, in which case the remaining components of the indicator can be portable, handheld or can be fixed.

For example, the detector and processor component can be positioned at a location remote from the container, e.g., within a control room of the like, to facilitate monitoring or measuring the volume within the tank or container from within the control room. In such case, the acoustic volume indicator can be configured having alarm setpoints to provide a visual and/or audible signal or alert should a volume outside of the setpoints be measured for a particular container. Alternatively, the detector and processor component can be a portable or handheld unit, such as that described above, that can be carried with a user in the field to each tank or container location to be measured. Accordingly, it is to be understood that the detector and signal processors of acoustic volume indicators of this invention can be provided in configurations best suited for the particular volume measurement application.

For example, a detector and processor used with the acoustic volume indicator of this invention can be configured to receive response signals from a single resonating sensor or a number of different resonating sensor means for the purpose of determining the measured volume of one or a number of different tanks that are connected thereto, depending on the particular application.

FIG. 6 illustrates an example acoustic volume indicator 104 of this invention comprising a container 106 that may be configured to accommodate a volume of liquid or gas. Additionally, the container 106 may or may not comprise a pressurized bladder, e.g., be provided in the form of a surge suppressor. A resonating means 108, e.g., in the form of a solenoid impactor, is attached to an outside wall surface 110 of the container 106, and a sensing means 112 is also attached the wall surface 110, e.g., near the resonating means 108. If desired, a pressure transmitter 114 can also be attached to the container for the purpose of measuring the pressure within the container, e.g., the pressure within the bladder when the container is provided in the form of a surge suppressor.

A computer 116 comprising the software based waveform analysis program described above is connected with a suitable AC or DC power source 117, and a signal conditioner and/or an external sound card 118 is connected to the computer to receive a signal from the sensing means 112. The computer 116 can be used locally, e.g., within the field, near the container or can be used remotely from the container, e.g., within a control room or the like. The sensing means 112 is connected to the signal conditioner and/or external sound card 118 by a suitable signal transfer cable 120.

A relay box 122 is also connected with the computer 116, and is used to send an actuating signal to the resonating means 108 via a suitable signal generating cable 124. The relay box is powered by an AC or DC power supply 125, and can also be configured to provide one or more alarm output signal 126 based on the container volume as determined by the computer software. In an example embodiment, the acoustic volume indicator is configured to provide a high volume and a low volume alarm that can be visual and/or audible in nature.

If the container 106 is provided in the form of a surge suppressor, containing a pressurized bladder, an input box 128 may be connected with the computer 116 and used for the purpose of transmitting a signal to the computer from the pressure transmitter 114. The input box 128 is connected with the pressure transmitter 114 in such an embodiment by a suitable signal transfer cable 130.

Configured in this manner, the acoustic volume indicator can be used remotely from the container for the purpose of measuring the gas or liquid volume container therein and/or for monitoring the pressure of an elastomeric bladder when the container being measured is a surge suppressor.

A feature of acoustic volume indicators of this invention is that they enable accurate measurement of a liquid or gas volume within a container in a manner that does not involve invading the container volume, which is important for volume measurements in such pressurized containers as hydraulic surge suppressors. Additionally, the ability to determine liquid or gas volume noninvasively eliminates the possibility of having any unintended liquid or gas leakage due to the presence of a leak path formed from an invasive measuring member, thereby reducing or eliminating the possibility of a health, safety or environmental risk associated therewith.

A further feature of acoustic volume indicators of this invention is that they can be used to measure the volume of a container comprising mixture of liquid and solids, such as in a sewage application. Another advantage is that such acoustic volume indicators of this invention can be used to determine not only the volume of liquid within a liquid surge suppressor, but to determine the precharge of a bladder disposed therein without having to take the suppressor offline, thereby saving time and costs. Another advantage of the acoustic volume indicator of this invention is that it is not sensitive to temperature, pressure, installation connections or fluid specific gravity. As long as these parameters are constant, the calibrations will produce a constant result.

The above-described embodiments of the present invention are merely descriptive of its principles and are not to be considered limiting. The scope of the present invention instead shall be determined from the scope of any claims in a corresponding non-provisional application, including their equivalents.

What is claimed is:

1. An acoustic volume indicator comprising:
   a resonating means positioned adjacent a wall of a container comprising a volume of liquid or gas therein for impacting and vibrating the container wall;
   a resonating detecting means positioned adjacent the container wall for receiving vibration data provided by the container after the resonating means is actuated, and for providing a data signal;
   a processing means for receiving the data signal, converting the data signal to frequency information, comparing the frequency information to stored frequency and volume information, and producing an output indicative of a measured volume within the container; and
   an indicator for displaying the output in a visual or audible form.

2. The acoustic volume indicator as recited in claim 1 wherein the processing means comprises a electrical microprocessor device.

3. The acoustic volume indicator as recited in claim 2 wherein the electrical microprocessor device includes a housing having a visual display comprising a number of light sources that are configured to represent a different volume in the container, wherein the electrical microprocessor device output operates one or more of the light sources to provide a visual indication of the measured volume.

4. The acoustic volume indicator as recited in claim 1 wherein the processing means comprises a computer and a computer program that is configured to analyze the frequency information to determine a peak frequency, compare the peak frequency to the frequency and volume information, and provide the output indicative of the measured volume within the container.

5. The acoustic volume indicator as recited in claim 4 wherein the indicator is a video display device.

6. The acoustic volume indicator as recited in claim 4 wherein the computer is provided in the form of a portable or handheld device.

7. The acoustic volume indicator as recited in claim 1 wherein the container comprises a volume of liquid therein.

8. The acoustic volume indicator as recited in claim 7 wherein the container includes a pressurized gas-filled bladder disposed therein.

9. The acoustic volume indicator as recited in claim 1 wherein the container comprises a volume of gas therein.

10. An acoustic volume indicator comprising:
   a contactor positioned adjacent a wall of a liquid or gas container to momentarily contact the wall to make the wall vibrate;
   a detector in contact with the wall for receiving vibration information from the wall;
   a processor for receiving a data signal from the detector, converting the data signal to frequency information, comparing the frequency information to characteristic frequency and volume information for the container to determine a volume in the container, and providing an output signal indicating the determined volume; and
   an indicator for providing a visual or audio indication of the determined volume.

11. The acoustic volume indicator as recited in claim 10 wherein the processor comprises a housing including a plurality of indicators, and an input for receiving the data signal, wherein the processor is configured so that each indicator represents a volume level in the container, and wherein the processor provides its output signal to one or more of the indicators to indicate the determined volume.

12. The acoustic volume indicator as recited in claim 10 wherein the processor comprises a computer and a computer program configured to analyze the frequency information, compare the frequency information with the characteristic frequency and volume information, wherein the indicator in the form of a display device that visually displays the determined volume.

13. The acoustic volume indicator as recited in claim 12 wherein the computer program comprises a spectrum analyzer that analyzes the frequency information to determine a frequency peak, wherein the frequency peak is compared with the characteristic frequency and volume information to determine the volume in the container.

14. The acoustic volume indicator as recited in claim 12 wherein the computer is a portable or handheld device.

15. A noninvasive method for measuring a volume of liquid or gas within a container comprising the steps of:
   vibrating a wall of the container by striking an outside wall surface of the container with a contactor;
   receiving vibration data from the liquid container by using a detector placed adjacent the container outside wall surface;
   converting the vibration data into frequency information;
   comparing the frequency information to characteristic frequency and volume data for the container to determine a liquid or gas volume within the container; and
   providing an output indicative of the determined liquid or gas volume.

16. The method as recited in claim 15 wherein the steps of comparing and providing are performed by a electrical microprocessor device comprising a housing and a number of indicators that are configured to represent a different container volume, wherein the microprocessor device is configured to provide an output that causes activation of one of the indicators.

17. The method as recited in claim 15 further comprising, after the step of converting, analyzing the frequency information to determine a frequency peak.

18. The method as recited in claim 15 wherein the steps of converting, converting, and providing are performed by a computer and a computer program that is configured to analyze the frequency information and compare the frequency information with the characteristic frequency and volume information, wherein the computer provides an output to a display device for visually displaying the determined volume.

19. The method as recited in claim 18 wherein the computer program performs a spectrum analysis of the frequency information to determine a frequency peak, and wherein the frequency peak is compared with the characteristic frequency and volume information to determine the volume in the container.

* * * * *